United States Patent
Willis et al.

(10) Patent No.: US 10,182,923 B2
(45) Date of Patent: Jan. 22, 2019

(54) SPINAL IMPLANT WITH POROUS AND SOLID SURFACES

(71) Applicant: Stryker European Holdings I, LLC, Kalamazoo, MI (US)

(72) Inventors: Steven Willis, Mahwah, NJ (US); Justyna Zielinska, Linden, NJ (US); Robin Stamp, Montclair, NJ (US); Chau Ngo, Secaucus, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 4 days.

(21) Appl. No.: 14/994,749

(22) Filed: Jan. 13, 2016

(65) Prior Publication Data
US 2016/0199193 A1    Jul. 14, 2016

Related U.S. Application Data

(60) Provisional application No. 62/103,276, filed on Jan. 14, 2015.

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/3094* (2013.01); *A61F 2/44* (2013.01); *A61F 2/4455* (2013.01); *A61F 2/4611* (2013.01); *A61F 2002/30013* (2013.01); *A61F 2002/3092* (2013.01); *A61F 2002/3093* (2013.01); *A61F 2002/30904* (2013.01); *A61F 2002/30985* (2013.01); *A61F 2002/4475* (2013.01)

(58) Field of Classification Search
CPC .......... A61F 2/447; A61F 2/3094; A61F 2/44; A61F 2002/3092; A61F 2002/30904; A61F 2002/3093; A61F 2002/4475
See application file for complete search history.

(56) References Cited

U.S. PATENT DOCUMENTS

| | | |
|---|---|---|
| 3,486,505 A | 12/1969 | Morrison |
| 3,641,590 A | 2/1972 | Michele |
| 3,852,045 A | 12/1974 | Wheeler et al. |
| 3,855,638 A | 12/1974 | Pilliar |
| 4,047,524 A | 9/1977 | Hall |
| 4,501,269 A | 2/1985 | Bagby |

(Continued)

FOREIGN PATENT DOCUMENTS

| | | |
|---|---|---|
| DE | 10052008 C1 | 8/2002 |
| DE | 202013007361 U1 | 3/2014 |

(Continued)

OTHER PUBLICATIONS

European Search Report for Application No. 16170075 dated Oct. 21, 2016.

(Continued)

*Primary Examiner* — Ellen C Hammond
(74) *Attorney, Agent, or Firm* — Lerner, David, Littenberg, Krumholz & Mentlik, LLP

(57) ABSTRACT

A spinal implant including porous and solid portions is disclosed. The implant includes porous portions on upper and lower surfaces and in an interior thereof. Methods of manufacturing and implanting such implants are also disclosed.

13 Claims, 15 Drawing Sheets

(56) References Cited

U.S. PATENT DOCUMENTS

| | | |
|---|---|---|
| 4,612,160 A | 9/1986 | Donlevy et al. |
| 4,653,489 A | 3/1987 | Tronzo |
| 4,681,589 A | 7/1987 | Tronzo |
| 4,718,914 A * | 1/1988 | Frey .......................... A61F 2/32 623/23.32 |
| 4,743,262 A | 5/1988 | Tronzo |
| 4,820,305 A | 4/1989 | Harms et al. |
| 4,834,757 A | 5/1989 | Brantigan |
| 4,946,378 A | 8/1990 | Hirayama et al. |
| 5,071,437 A | 12/1991 | Steffee |
| 5,156,628 A * | 10/1992 | Kranz ................. A61F 2/30771 623/23.33 |
| 5,192,327 A | 3/1993 | Brantigan |
| 5,263,986 A | 11/1993 | Noiles et al. |
| 5,306,309 A | 4/1994 | Wagner et al. |
| 5,314,477 A | 5/1994 | Marnay |
| 5,370,692 A | 12/1994 | Fink et al. |
| 5,431,658 A | 7/1995 | Moskovich |
| 5,443,514 A | 8/1995 | Steffee |
| 5,443,515 A | 8/1995 | Cohen et al. |
| 5,458,643 A | 10/1995 | Oka et al. |
| 5,504,300 A | 4/1996 | Devanathan et al. |
| 5,507,816 A | 4/1996 | Bullivant |
| 5,514,180 A | 5/1996 | Heggeness et al. |
| 5,609,635 A | 3/1997 | Michelson |
| 5,672,284 A | 9/1997 | Devanathan et al. |
| 5,683,394 A | 11/1997 | Rinner |
| 5,702,449 A | 12/1997 | McKay |
| 5,702,455 A | 12/1997 | Saggar |
| 5,709,683 A | 1/1998 | Bagby |
| 5,713,899 A | 2/1998 | Marnay et al. |
| 5,723,011 A | 3/1998 | Devanathan et al. |
| 5,734,959 A | 3/1998 | Krebs et al. |
| 5,768,134 A | 6/1998 | Swaelens et al. |
| 5,885,299 A | 3/1999 | Winslow et al. |
| 5,893,889 A | 4/1999 | Harrington |
| 5,961,554 A | 10/1999 | Janson et al. |
| 6,039,762 A | 3/2000 | McKay |
| 6,096,080 A | 8/2000 | Nicholson et al. |
| 6,113,638 A | 9/2000 | Williams et al. |
| 6,120,503 A | 9/2000 | Michelson |
| 6,206,924 B1 | 3/2001 | Timm |
| 6,235,059 B1 | 5/2001 | Benezech et al. |
| 6,241,769 B1 | 6/2001 | Nicholson et al. |
| 6,241,771 B1 | 6/2001 | Gresser et al. |
| 6,325,805 B1 | 12/2001 | Ogilvie et al. |
| 6,336,928 B1 | 1/2002 | Guerin et al. |
| 6,364,880 B1 | 4/2002 | Michelson |
| 6,432,107 B1 | 8/2002 | Ferree |
| 6,447,524 B1 | 9/2002 | Knodel et al. |
| 6,447,546 B1 | 9/2002 | Bramlet et al. |
| 6,458,158 B1 | 10/2002 | Anderson et al. |
| 6,471,725 B1 | 10/2002 | Ralph et al. |
| 6,485,521 B1 | 11/2002 | Say et al. |
| 6,533,818 B1 | 3/2003 | Weber et al. |
| 6,569,201 B2 | 5/2003 | Moumene et al. |
| 6,572,654 B1 | 6/2003 | Santilli |
| 6,582,468 B1 | 6/2003 | Gauchet |
| 6,623,525 B2 | 9/2003 | Ralph et al. |
| 6,673,075 B2 | 1/2004 | Santilli |
| 6,679,887 B2 | 1/2004 | Nicholson et al. |
| 6,716,245 B2 | 4/2004 | Pasquet et al. |
| 6,726,720 B2 | 4/2004 | Ross et al. |
| 6,740,118 B2 | 5/2004 | Eisermann et al. |
| 6,740,186 B2 | 5/2004 | Hawkins et al. |
| 6,743,256 B2 | 6/2004 | Mason |
| 6,767,367 B1 | 7/2004 | Michelson |
| 6,790,233 B2 | 9/2004 | Brodke et al. |
| 6,800,093 B2 | 10/2004 | Nicholson et al. |
| 6,843,805 B2 | 1/2005 | Webb et al. |
| 6,863,689 B2 | 3/2005 | Ralph et al. |
| 6,945,448 B2 | 9/2005 | Medlin et al. |
| 6,970,233 B2 | 11/2005 | Blatchford |
| 7,048,766 B2 | 5/2006 | Ferree |
| 7,056,344 B2 | 6/2006 | Ruppert et al. |
| 7,056,345 B2 | 6/2006 | Kuslich |
| 7,060,097 B2 | 6/2006 | Fraser et al. |
| 7,128,761 B2 | 10/2006 | Kuras et al. |
| 7,135,042 B2 | 11/2006 | Stoll |
| 7,204,852 B2 | 4/2007 | Marnay et al. |
| 7,235,101 B2 | 6/2007 | Berry et al. |
| 7,238,203 B2 | 7/2007 | Bagga et al. |
| 7,241,313 B2 | 7/2007 | Unwin et al. |
| 7,255,713 B2 | 8/2007 | Malek |
| 7,320,707 B2 | 1/2008 | Zucherman et al. |
| 7,331,995 B2 | 2/2008 | Eisermann et al. |
| 7,364,589 B2 | 4/2008 | Eisermann |
| 7,497,876 B2 | 3/2009 | Tuke et al. |
| 7,501,073 B2 | 3/2009 | Wen et al. |
| 7,503,934 B2 | 3/2009 | Eisermann et al. |
| 7,503,935 B2 | 3/2009 | Zucherman et al. |
| 7,537,664 B2 | 5/2009 | O'Neill et al. |
| 7,563,284 B2 | 7/2009 | Coppes et al. |
| 7,588,600 B2 | 9/2009 | Benzel et al. |
| 7,594,931 B2 | 9/2009 | Louis et al. |
| 7,611,538 B2 | 11/2009 | Belliard et al. |
| 7,635,447 B2 | 12/2009 | Hamman et al. |
| 7,658,766 B2 | 2/2010 | Melkent et al. |
| 7,662,186 B2 | 2/2010 | Bagga et al. |
| 7,670,375 B2 | 3/2010 | Schaller |
| 7,695,516 B2 | 4/2010 | Zeegers |
| 7,749,271 B2 | 7/2010 | Fischer et al. |
| 7,763,076 B2 | 7/2010 | Navarro et al. |
| 7,842,088 B2 | 11/2010 | Rashbaum et al. |
| 7,883,661 B2 | 2/2011 | Hamman et al. |
| 7,896,919 B2 | 3/2011 | Belliard et al. |
| 7,918,382 B2 | 4/2011 | Charlebois et al. |
| 7,922,765 B2 | 4/2011 | Reiley |
| 8,021,403 B2 | 9/2011 | Wall et al. |
| 8,034,076 B2 | 10/2011 | Criscuolo et al. |
| 8,100,974 B2 | 1/2012 | Duggal et al. |
| 8,147,861 B2 | 4/2012 | Jones et al. |
| 8,191,760 B2 | 6/2012 | Charlebois et al. |
| 8,202,305 B2 | 6/2012 | Reiley |
| 8,231,676 B2 | 7/2012 | Trudeau et al. |
| 8,262,737 B2 | 9/2012 | Bagga et al. |
| 8,266,780 B2 | 9/2012 | Bollinger et al. |
| 8,268,100 B2 | 9/2012 | O'Neill et al. |
| 8,303,879 B2 | 11/2012 | Bertele et al. |
| 8,343,224 B2 | 1/2013 | Lynn et al. |
| 8,349,015 B2 | 1/2013 | Bae et al. |
| 8,361,150 B2 | 1/2013 | Zhang et al. |
| 8,361,153 B2 | 1/2013 | Ralph et al. |
| 8,361,380 B2 | 1/2013 | Hamman et al. |
| 8,388,667 B2 | 3/2013 | Reiley et al. |
| 8,403,991 B2 | 3/2013 | Ullrich, Jr. et al. |
| 8,414,648 B2 | 4/2013 | Reiley |
| 8,414,650 B2 | 4/2013 | Bertele et al. |
| 8,414,654 B1 | 4/2013 | Ganey |
| 8,414,820 B2 | 4/2013 | Bertele et al. |
| 8,425,570 B2 | 4/2013 | Reiley |
| 8,425,604 B2 | 4/2013 | Trieu |
| 8,430,930 B2 | 4/2013 | Hunt |
| 8,435,301 B2 | 5/2013 | Gerber et al. |
| 8,435,302 B2 | 5/2013 | Ulrich, Jr. et al. |
| 8,444,693 B2 | 5/2013 | Reiley |
| 8,470,004 B2 | 6/2013 | Reiley |
| 8,470,042 B2 | 6/2013 | Zhang et al. |
| 8,480,749 B2 | 7/2013 | Ullrich, Jr. et al. |
| 8,496,710 B2 | 7/2013 | Bagga et al. |
| 8,530,560 B2 | 9/2013 | Kerr et al. |
| 8,545,568 B2 | 10/2013 | Ulrich, Jr. et al. |
| 8,551,173 B2 | 10/2013 | Lechmann et al. |
| 8,551,176 B2 | 10/2013 | Ullrich, Jr. et al. |
| 8,556,981 B2 | 10/2013 | Jones et al. |
| 8,562,684 B2 | 10/2013 | Ullrich, Jr. et al. |
| 8,562,685 B2 | 10/2013 | Ullrich, Jr. et al. |
| 8,585,765 B2 | 11/2013 | Ullrich, Jr. et al. |
| 8,585,766 B2 | 11/2013 | Ullrich, Jr. et al. |
| 8,585,767 B2 | 11/2013 | Ullrich, Jr. et al. |
| 8,591,590 B2 | 11/2013 | Ullrich, Jr. et al. |
| 8,617,248 B2 | 12/2013 | Ullrich, Jr. et al. |
| 8,632,604 B2 | 1/2014 | Brooks |
| 8,673,016 B2 | 3/2014 | Liu |

(56) References Cited

U.S. PATENT DOCUMENTS

| | | |
|---|---|---|
| 8,734,462 B2 | 5/2014 | Reiley et al. |
| 8,747,412 B2 | 6/2014 | Bae et al. |
| 8,758,442 B2 | 6/2014 | Ullrich, Jr. et al. |
| 8,758,443 B2 | 6/2014 | Ullrich, Jr. et al. |
| 8,814,939 B2 | 8/2014 | Ullrich, Jr. et al. |
| 8,814,978 B2 | 8/2014 | Hamman et al. |
| 8,827,986 B2 | 9/2014 | Shachar et al. |
| 8,834,571 B2 | 9/2014 | Bagga et al. |
| 8,840,623 B2 | 9/2014 | Reiley |
| 8,845,736 B2 | 9/2014 | Zhang et al. |
| 8,864,831 B2 | 10/2014 | Lee et al. |
| 8,906,093 B2 | 12/2014 | Malone |
| 8,906,095 B2 | 12/2014 | Christensen et al. |
| 8,940,053 B2 | 1/2015 | Ullrich, Jr. et al. |
| 8,979,934 B2 | 3/2015 | Kirschman |
| 8,985,430 B2 | 3/2015 | Charlebois et al. |
| 8,992,619 B2 | 3/2015 | Patterson et al. |
| 9,089,428 B2 | 7/2015 | Bertele et al. |
| 9,135,374 B2 | 9/2015 | Jones et al. |
| 9,180,010 B2 | 11/2015 | Dong et al. |
| 2002/0004683 A1 | 1/2002 | Michelson |
| 2002/0035400 A1 | 3/2002 | Bryan et al. |
| 2002/0165613 A1 | 11/2002 | Lin et al. |
| 2003/0045940 A1 | 3/2003 | Eberlein et al. |
| 2003/0055505 A1 | 3/2003 | Sicotte et al. |
| 2003/0195517 A1 | 10/2003 | Michelson |
| 2003/0195632 A1 | 10/2003 | Foley et al. |
| 2004/0059318 A1 | 3/2004 | Zhang et al. |
| 2004/0117022 A1 | 6/2004 | Marnay et al. |
| 2004/0133279 A1 | 7/2004 | Krueger et al. |
| 2004/0148028 A1 | 7/2004 | Ferree et al. |
| 2004/0176853 A1 | 9/2004 | Sennett et al. |
| 2004/0193271 A1 | 9/2004 | Fraser et al. |
| 2004/0199254 A1 | 10/2004 | Louis et al. |
| 2004/0220668 A1 | 11/2004 | Eisermann et al. |
| 2004/0220670 A1 | 11/2004 | Eisermann et al. |
| 2004/0230307 A1 | 11/2004 | Eisermann |
| 2004/0260286 A1 | 12/2004 | Ferree |
| 2005/0004672 A1 | 1/2005 | Pafford et al. |
| 2005/0033435 A1 | 2/2005 | Belliard et al. |
| 2005/0043802 A1 | 2/2005 | Eisermann et al. |
| 2005/0060034 A1 | 3/2005 | Berry et al. |
| 2005/0123672 A1 | 6/2005 | Justin et al. |
| 2005/0149192 A1 | 7/2005 | Zucherman et al. |
| 2005/0149193 A1 | 7/2005 | Zucherman et al. |
| 2005/0165408 A1 | 7/2005 | Puno et al. |
| 2005/0177238 A1 | 8/2005 | Khandkar et al. |
| 2005/0192586 A1 | 9/2005 | Zucherman et al. |
| 2006/0004453 A1 | 1/2006 | Bartish et al. |
| 2006/0085071 A1 | 4/2006 | Lechmann et al. |
| 2006/0089656 A1 | 4/2006 | Allard et al. |
| 2006/0116769 A1 | 6/2006 | Marnay et al. |
| 2006/0129238 A1 | 6/2006 | Paltzer |
| 2006/0136063 A1 | 6/2006 | Zeegers |
| 2006/0147332 A1 | 7/2006 | Jones et al. |
| 2006/0178745 A1 | 8/2006 | Bartish et al. |
| 2006/0212121 A1 | 9/2006 | Ferree |
| 2007/0050032 A1 | 3/2007 | Gittings et al. |
| 2007/0050033 A1 | 3/2007 | Reo et al. |
| 2007/0055378 A1 | 3/2007 | Ankney et al. |
| 2007/0073404 A1 | 3/2007 | Rashbaum et al. |
| 2007/0118145 A1 | 5/2007 | Fischer et al. |
| 2007/0142914 A1 | 6/2007 | Jones et al. |
| 2007/0173940 A1 | 7/2007 | Hestad et al. |
| 2007/0233244 A1 | 10/2007 | Lopez et al. |
| 2007/0233261 A1 | 10/2007 | Lopez et al. |
| 2007/0239278 A1 | 10/2007 | Heinz |
| 2007/0270968 A1 | 11/2007 | Baynham et al. |
| 2008/0004709 A1 | 1/2008 | O'Neill et al. |
| 2008/0015702 A1 | 1/2008 | Lakin et al. |
| 2008/0051901 A1 | 2/2008 | de Villiers et al. |
| 2008/0051902 A1 | 2/2008 | Dwyer |
| 2008/0097435 A1 | 4/2008 | DeRidder et al. |
| 2008/0109005 A1 | 5/2008 | Trudeau et al. |
| 2008/0154377 A1 | 6/2008 | Voellmicke |
| 2008/0161927 A1* | 7/2008 | Savage ............... A61F 2/4455 623/17.16 |
| 2008/0183292 A1 | 7/2008 | Trieu |
| 2008/0249575 A1 | 10/2008 | Waugh et al. |
| 2008/0262623 A1 | 10/2008 | Bagga et al. |
| 2008/0269756 A1 | 10/2008 | Tomko et al. |
| 2008/0306595 A1 | 12/2008 | McLeod et al. |
| 2009/0005870 A1 | 1/2009 | Hawkins et al. |
| 2009/0088849 A1 | 4/2009 | Armstrong et al. |
| 2009/0093885 A1 | 4/2009 | Levieux et al. |
| 2009/0112323 A1 | 4/2009 | Hestad et al. |
| 2009/0138015 A1 | 5/2009 | Conner et al. |
| 2009/0164020 A1 | 6/2009 | Janowski et al. |
| 2009/0240333 A1 | 9/2009 | Trudeau et al. |
| 2010/0004747 A1 | 1/2010 | Lin |
| 2010/0042218 A1 | 2/2010 | Nebosky et al. |
| 2010/0042221 A1 | 2/2010 | Boyd |
| 2010/0076559 A1 | 3/2010 | Bagga et al. |
| 2010/0094426 A1 | 4/2010 | Grohowski, Jr. et al. |
| 2010/0137990 A1 | 6/2010 | Apatsidis et al. |
| 2010/0185292 A1 | 7/2010 | Hochschuler et al. |
| 2010/0211119 A1 | 8/2010 | Refai et al. |
| 2010/0222750 A1 | 9/2010 | Cheng |
| 2010/0256773 A1 | 10/2010 | Thijs et al. |
| 2010/0262244 A1 | 10/2010 | Savage-Erickson et al. |
| 2010/0268343 A1 | 10/2010 | Dewey et al. |
| 2011/0004307 A1 | 1/2011 | Ahn et al. |
| 2011/0029081 A1 | 2/2011 | Malone |
| 2011/0071635 A1 | 3/2011 | Zhang et al. |
| 2011/0092948 A1 | 4/2011 | Shachar et al. |
| 2011/0160866 A1 | 6/2011 | Laurence et al. |
| 2011/0196494 A1 | 8/2011 | Yedlicka et al. |
| 2011/0196495 A1 | 8/2011 | Hunt |
| 2011/0282392 A1 | 11/2011 | Murphy et al. |
| 2011/0282454 A1 | 11/2011 | Ullrich, Jr. et al. |
| 2011/0313532 A1 | 12/2011 | Hunt |
| 2012/0078373 A1 | 3/2012 | Gamache et al. |
| 2012/0253406 A1 | 10/2012 | Bae et al. |
| 2012/0265306 A1 | 10/2012 | Trieu |
| 2012/0277876 A1 | 11/2012 | Ullrich, Jr. et al. |
| 2012/0303127 A1 | 11/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0330420 A1 | 12/2012 | Brodke et al. |
| 2013/0030529 A1 | 1/2013 | Hunt |
| 2013/0123925 A1 | 5/2013 | Patterson et al. |
| 2013/0123935 A1 | 5/2013 | Hunt et al. |
| 2013/0158672 A1 | 6/2013 | Hunt |
| 2013/0218282 A1 | 8/2013 | Hunt |
| 2013/0226302 A1 | 8/2013 | Bae et al. |
| 2013/0274886 A1 | 10/2013 | Matsumoto et al. |
| 2013/0282122 A1 | 10/2013 | Ullrich, Jr. et al. |
| 2013/0292357 A1 | 11/2013 | Ullrich, Jr. et al. |
| 2013/0304218 A1 | 11/2013 | Ullrich, Jr. et al. |
| 2013/0306591 A1 | 11/2013 | Ullrich, Jr. et al. |
| 2013/0338777 A1 | 12/2013 | Bagga et al. |
| 2014/0025169 A1 | 1/2014 | Lechmann et al. |
| 2014/0031942 A1 | 1/2014 | Ullrich, Jr. et al. |
| 2014/0046449 A1 | 2/2014 | Ullrich, Jr. et al. |
| 2014/0114415 A1 | 4/2014 | Tyber |
| 2014/0114421 A1 | 4/2014 | Ullrich, Jr. et al. |
| 2014/0121776 A1 | 5/2014 | Hunt |
| 2014/0277461 A1 | 9/2014 | Nebosky et al. |
| 2014/0277491 A1 | 9/2014 | Fang et al. |
| 2014/0277511 A1 | 9/2014 | Ullrich, Jr. et al. |
| 2014/0277512 A1 | 9/2014 | Ullrich, Jr. et al. |
| 2014/0288649 A1 | 9/2014 | Hunt |
| 2014/0288650 A1 | 9/2014 | Hunt |
| 2014/0350682 A1 | 11/2014 | Bagga et al. |
| 2015/0012100 A1 | 1/2015 | Ullrich, Jr. et al. |
| 2015/0018956 A1 | 1/2015 | Steinmann et al. |
| 2015/0045903 A1 | 2/2015 | Neal |
| 2015/0073422 A1 | 3/2015 | Chegini et al. |
| 2015/0157465 A1 | 6/2015 | Kirschman |
| 2015/0202047 A1 | 7/2015 | Patterson et al. |
| 2016/0038301 A1* | 2/2016 | Wickham ............... A61F 2/447 623/17.16 |

(56) References Cited

U.S. PATENT DOCUMENTS

FOREIGN PATENT DOCUMENTS

| | | | |
|---|---|---|---|
| EP | 0179695 A1 | 4/1986 | |
| EP | 0505634 A1 | 9/1992 | |
| EP | 1327423 A1 | 7/2003 | |
| EP | 1790298 A1 | 5/2007 | |
| EP | 1872746 A2 | 1/2008 | |
| FR | 2858546 A1 | 2/2005 | |
| WO | 03005939 A2 | 1/2003 | |
| WO | 03/039400 A2 | 5/2003 | |
| WO | 03053290 A1 | 7/2003 | |
| WO | 2003092507 A2 | 11/2003 | |
| WO | 2004071359 A1 | 8/2004 | |
| WO | 2004080355 A1 | 9/2004 | |
| WO | 2004108015 A2 | 12/2004 | |
| WO | 2005051243 A2 | 6/2005 | |
| WO | 2006033067 A3 | 3/2006 | |
| WO | 2006051547 A2 | 5/2006 | |
| WO | 2006074414 A2 | 7/2006 | |
| WO | 2006086494 A2 | 8/2006 | |
| WO | 2006121795 A2 | 11/2006 | |
| WO | 2007028098 A2 | 3/2007 | |
| WO | 2007087366 A2 | 8/2007 | |
| WO | 2008014453 A2 | 1/2008 | |
| WO | 2008021955 A2 | 2/2008 | |
| WO | 2009099559 A2 | 8/2009 | |
| WO | 2010021612 A1 | 2/2010 | |
| WO | 2010028045 A1 | 3/2010 | |
| WO | 2010121149 A2 | 10/2010 | |
| WO | 2013133729 A1 | 9/2013 | |
| WO | 2014018325 A1 | 1/2014 | |

OTHER PUBLICATIONS

Extended European Search Report for Application No. EP16171066 dated Dec. 14, 2016.
International Search Report and Written Opinion, PCT/US2010/22494, dated Oct. 25, 2010.
International Search Report and Writen Opinion, PCT/US2010/044988, dated Feb. 4, 2011.
International Search Report and Written Opinion for Application No. PCT/US2010/055259, dated Apr. 7, 2011.
Bobyn JD. Next generation porous metals forbiologic fixation. In: Glassman AH, Lachiewicz PF, Tanzer, M, eds. Orthopaedic Knowledge Update: Hip and Knee Reconstruction 4. Rosemont, IL: American Academy of Orthopaedic Surgeons; 2011:45-58.
European Search Report dated Sep. 26, 2012 for PCT/US2010022494.
Extended European Search Report for Application No. 14152779 dated Mar. 18, 2014.
Karageorgiou, V., and D. Kaplan. "Porosity of 3D Biomaterial Scaffolds and Osteogenesis." Biomaterials 26.27 (2005): 5474-491.
Hards, W. H. and M. Jasty (1985). "Bone ingrowth into porous coated canine acetabular replacements: the effect of pore size, apposition, and dislocation." Hip: 214-34.
Kujala, S. et al (2003): "Effect of porosity on the osteointegration and bone ingrowth of a weightbearing nickel-titanium bone graft substitute", Biomaterials, 24(25), Nov. 2003, pp. 4691-4697.
Callaghan, J. J. (1993). "The clinical results and basic science of total hip arthroplasty with porous-coated prostheses." J Bone Joint Surg Am 75(2): 299-310.
Wu, s et al (2013). Porous Ti6AI4V Cage Has Better Osseointegration and Less Micromotion Than a PEEK cage in Sheep Vertebral Fusion. Artificial organs 37(12).
Bobyn, J. D., G. J. Stackpool, S. A. Hacking, M. Tanzer, and J. J. Krygier. "Characteristics of Bone Ingrowth and Interface Mechanics of a New Porous Tantalum Biomaterial." The Journal of Bone and Joint Surgery81.5 (1999): 907-14.
Extended European Search Report for Application No. 15161713.1 dated Jun. 29, 2015.
U.S. Appl. No. 14/994,697, filed Jan. 13, 2016.
U.S. Appl. No. 14/994,749, filed Jan. 13, 2016.
Extended European Search Report for Application No. 16151374.2 dated Jun. 8, 2016.
Extended European Search Report for Application No. 16151375 dated Jun. 8, 2016.
Extended European Search Report for Application No. EP16189379 dated Jun. 6, 2017.
Extended European Search Report for Application No. EP16202603 dated May 31, 2017.

\* cited by examiner

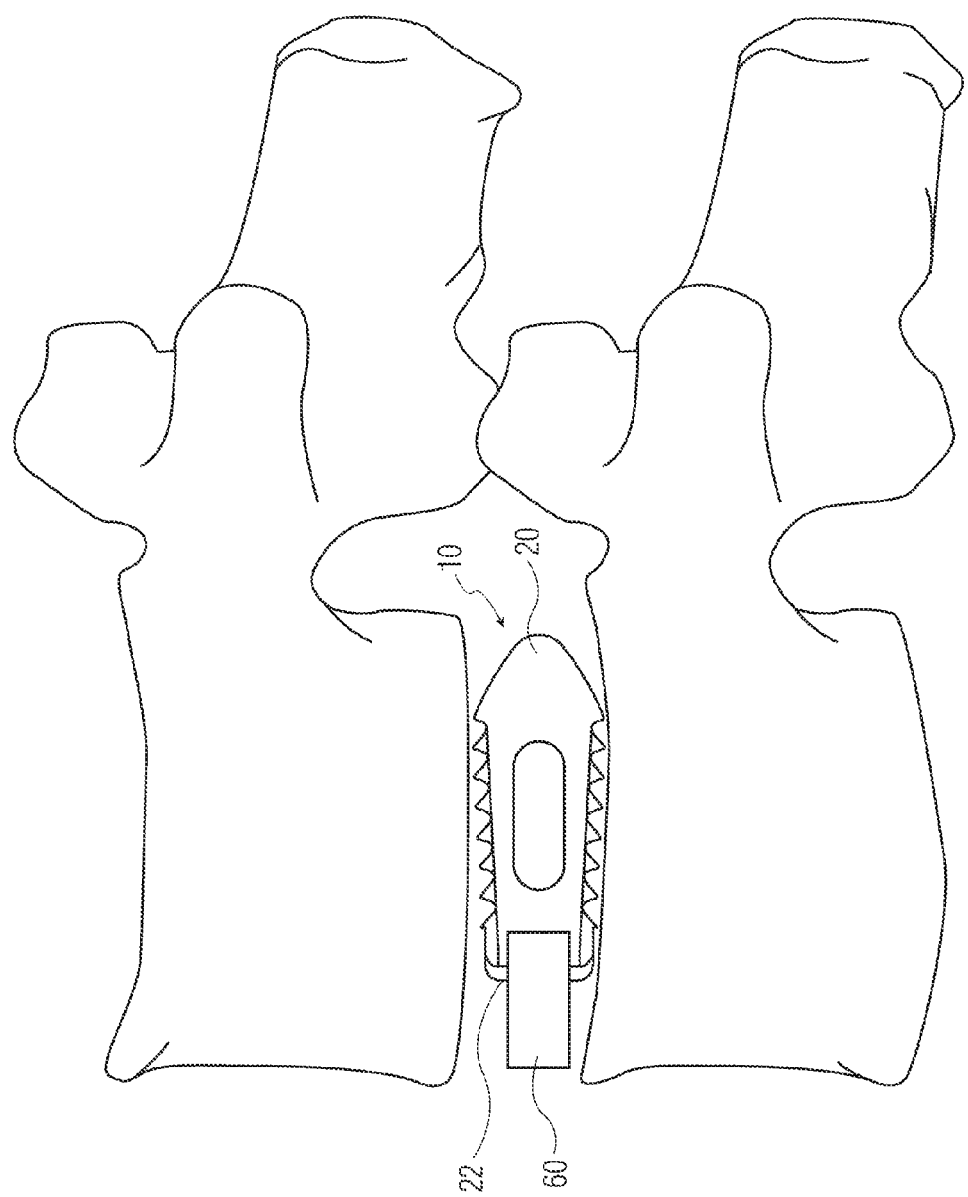

SPINAL IMPLANT WITH POROUS AND SOLID SURFACES

CROSS-REFERENCE TO RELATED APPLICATION

The present application claims the benefit of the filing date of U.S. Provisional Patent Application No. 62/103,276, filed Jan. 14, 2015, the disclosure of which is hereby incorporated herein by reference.

BACKGROUND OF THE INVENTION

The present invention relates to spinal surgery, namely, implants utilized in fusing adjacent intervertebral bodies or the replacement of a vertebral body.

Back pain can be caused by many different maladies, not the least of which are problems that directly impact the intervertebral discs of the spine. Typical disc issues include, inter alia, degeneration, bulging, herniation, thinning and abnormal movement. One method of treatment of such disc problems that has been widely utilized in the field of spinal surgery is a spinal fusion procedure, whereby an affected disc is removed, and the adjacent vertebral bodies are fused together through the use of interbody spacers, implants or the like. In some instances, it may also be necessary to remove and replace an entire vertebral body. This is often accomplished through the use of a larger implant that acts to fuse together the vertebral bodies adjacent the removed vertebral body.

The aforementioned implants often rely upon mechanical features to ensure engagement between the devices and the bone of the existing vertebral bodies. This coupled with the normal compressive load of the spine acts to keep the implant in place until bone can grow from the existing vertebral bodies into and through the implant. To encourage the bone growth, the implants are often pre-loaded with bone growth promoting material and thereafter placed into the spine. Bone growth promoting material may include naturally occurring bone, artificial materials or the like.

To further ensure a strong implant-bone connection, some existing implants include an area formed of porous material that allows bone to grow into it. Although there is little doubt that the bone growth into the implant is beneficial in maintaining an implant in place, these implants are often very difficult (and thusly, expensive) to manufacture. Additionally, existing implants that implement porous material do so in a limited manner. Often times, because of manufacturing or strength concerns or the like, the porous material is limited to a thin layer covering the upper and lower surfaces of the implant, which only allows for a small amount of bone to grow into the implant.

Therefore, there exists a need for an improved spinal implant that employs a significant amount of porous material, yet remains cost efficient and maintains the necessary strength required of a spinal implant.

BRIEF SUMMARY OF THE INVENTION

A first aspect of the present invention is a spinal implant including an upper surface including a first porous portion and first solid portion, a lower surface including a second porous portion and a second solid portion and a cavity formed through the upper and lower surfaces, the cavity including a third porous portion.

Other embodiments according to the first aspect may include a nose having a solid exterior, a hollow area and a porous region. At least one serration may be included on each of the upper and lower surfaces. The serration(s) may include a solid tip, a solid root and a porous section. The implant may further include first and second side walls extending between the upper and lower surfaces, the side walls including a solid exterior surface and a porous interior surface. The first and second side walls may each include lateral windows. The lateral windows may reduce the stiffness of the implant and may be tapered. The implant may also include a threaded opening at a rear end. Implants according to the present invention may be constructed of any material suitable for implantation in the body of a patient, for instance, a metal such as titanium. The implants can be configured for insertion from various aspects, e.g., a posterior approach, a lateral approach or an anterior approach. The implant may include a nose that facilitates the insertion of the implant in a first orientation and rotation to a second orientation. The implant may be constructed from an additive manufacturing process, and may be machined to create smooth surfaces.

BRIEF DESCRIPTION OF THE DRAWINGS

A more complete appreciation of the subject matter of the present invention and of the various advantages thereof can be realized by reference to the following detailed description in which reference is made to the accompanying drawings in which:

FIG. 10 is a fluoroscopic view of an implanted implant of FIG. 1.

DETAILED DESCRIPTION

Figure 1:
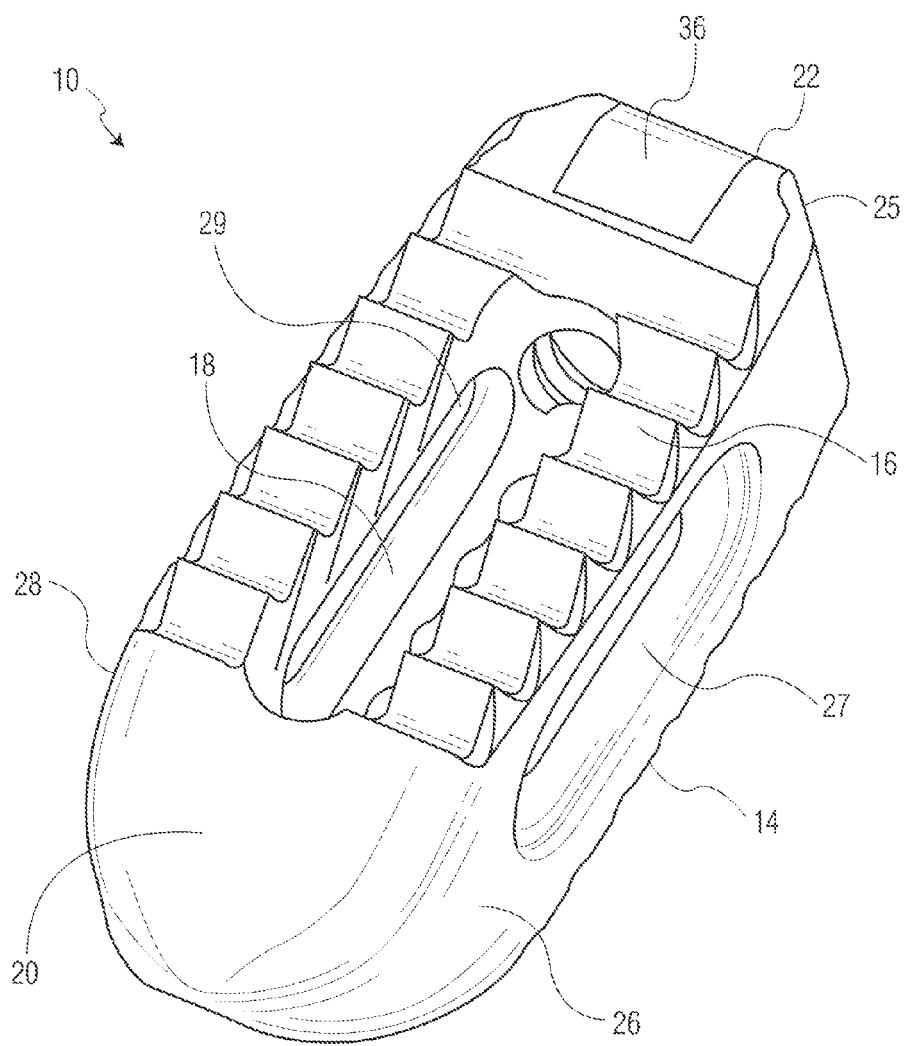
FIG. 1 is a front perspective view of an implant according to one embodiment of the present invention.
Figure 2A:
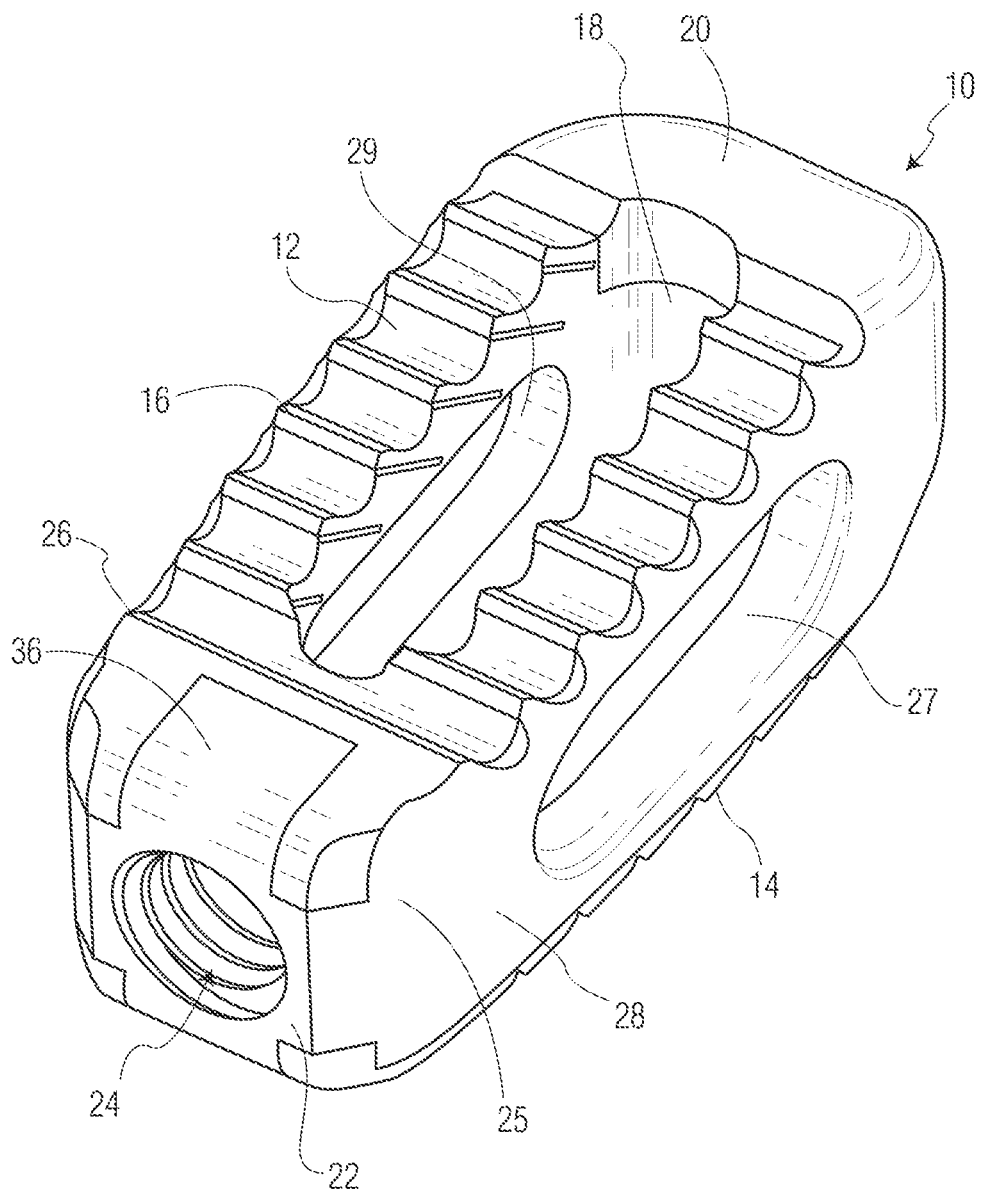
FIGS. 2A and 2B are rear perspective views of the implant of FIG. 1.
Figure 2B:
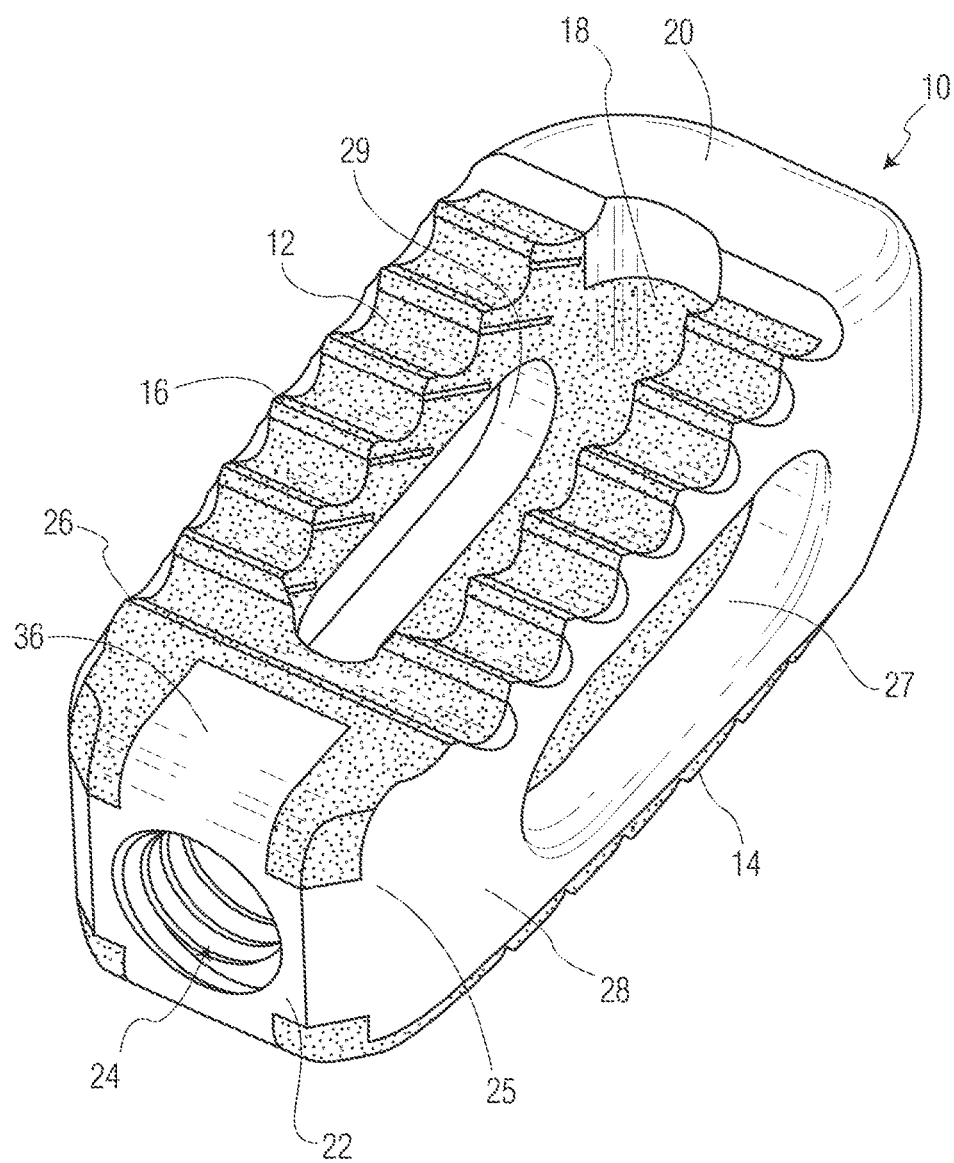
Figure 3:
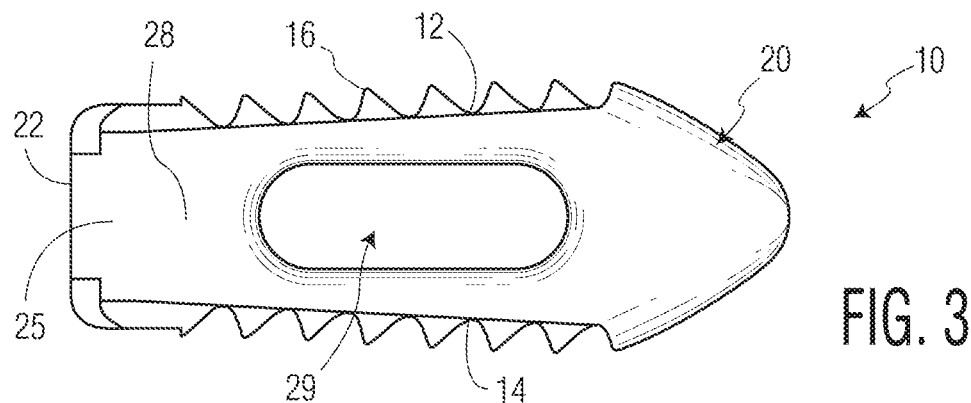
FIG. 3 is a side view of the implant of FIG. 1.
Figure 4A:
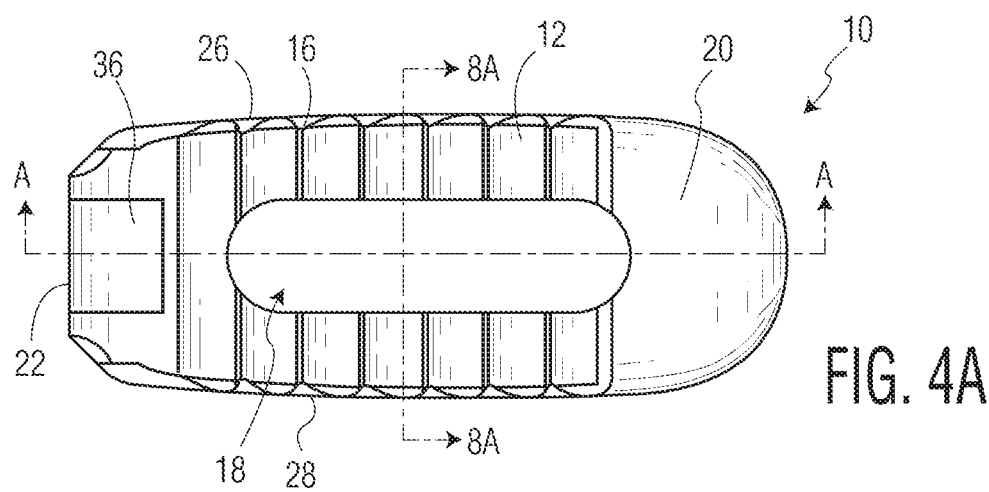
FIGS. 4A and 4B are top views of the implant of FIG. 1.
Figure 4B:
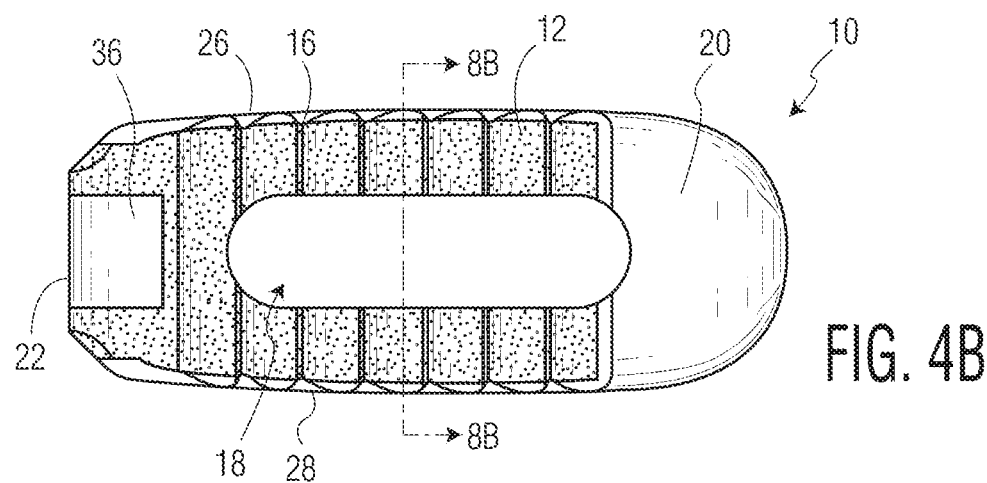
Figure 5:
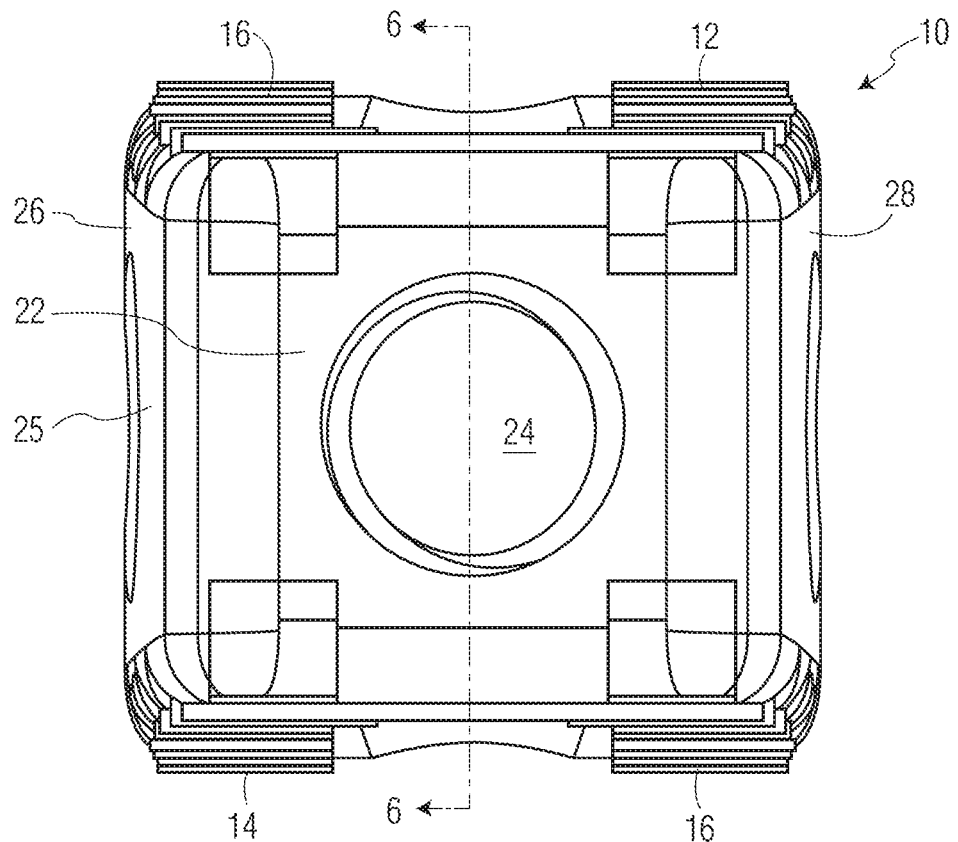
FIG. 5 is a rear view of the implant of FIG. 1.

An implant 10 according to a first embodiment of the present invention is depicted in FIGS. 1-10. Implant 10 is shown as an implant suitable for implantation from a posterior approach. However, as will be readily apparent from the below discussion pertaining to other embodiments, the present invention is not limited to any particular type of implant design. Rather, it is contemplated that certain features of the present invention can be implemented in different types of implants. For instance, implants according to the present invention can be adapted for implantation from anterior or lateral aspects of the patient, as will be discussed below. Moreover, although disclosed as being constructed of metallic materials, it is contemplated that implants according to the present invention may be constructed of polymeric materials such as PEEK or the like. Additionally, each of the embodiments shown in the drawings are designed for placement between adjacent vertebral bodies. However, it is contemplated that implants in accordance with the present invention may be designed for use as vertebral body replacements.

Implant 10 is shown including upper and lower surfaces 12 and 14, respectively. Each surface includes a plurality of serrations 16 at least covering a portion of the surface. While a specific serration design is depicted in the drawings and described in more detail below, many different serration designs can be employed. Implant 10 also includes a cavity 18 formed through a central portion of the implant and each of surfaces 12 and 14. Cavity 18 can be sized and shaped differently from what is shown and can be located in other locations of implant 10. Cavity 18 is preferably designed so that bone growth promoting materials can be contained therein to promote bone growth through the implant.

Implant 10 also includes a wedge nose 20, a rear end 22 with a threaded opening 24 and a chamfer interface 25, and sidewalls 26 and 28 through which lateral windows 27 and 29, respectively are formed. Wedge nose 20 is sized and shaped so as to distract vertebral bodies during insertion of the implant into the intervertebral space. Threaded opening 24 and chamfer interface 25 are configured to cooperate with an insertion tool (not shown in detail). Lateral windows 27 and 29 act to both reduce the stiffness of implant 10 and allow for visualization through the lateral aspect of the implant under fluoroscopy imaging. Of course, the specific sizes and shapes of these elements may vary in other embodiment implants in accordance with the present invention, including certain embodiments discussed below. For instance, certain of the surfaces of implant 10 are shown as smooth and rounded to reduce the potential for soft tissue damage during an implantation procedure, but can be configured differently.

Implant 10 is formed of both solid and porous portions. The porous portions are located on upper and lower surfaces 12, 14, as well as on certain of the internal surfaces of the implant, which allows for bone to grow into a significant portion of the implant. This can best be seen in FIGS. 2B, 4B, 8B, and 9A-9C, where the porous surfaces of implant 10 are shown with different shading. In one embodiment, the porous surfaces have an average pore diameter between 100-1000 microns with a 30-80% porosity, while a preferred embodiment would have a porosity between 55-65%. The porous surfaces may also have any thickness, for instance between 500-4500 microns, and preferably between 500-1500 microns. This results in a surface that is both strong enough for use in a spinal implant and maximizes bone growth potential. The porous portions of implant 10, as well as the solid portions, can be created through the use of a 3D printing process such as is disclosed in U.S. Pat. Nos. 7,537,664 and 8,147,861; U.S. Patent Application Publications Nos. 2006/0147332, 2007/0142914, 2008/0004709; and U.S. patent application Ser. Nos. 13/441,154 and 13/618,218, the disclosures of which are hereby incorporated by reference herein. It is also contemplated to form any porous portion via another known or hereafter developed procedure, such as laser etching.

Figure 6:
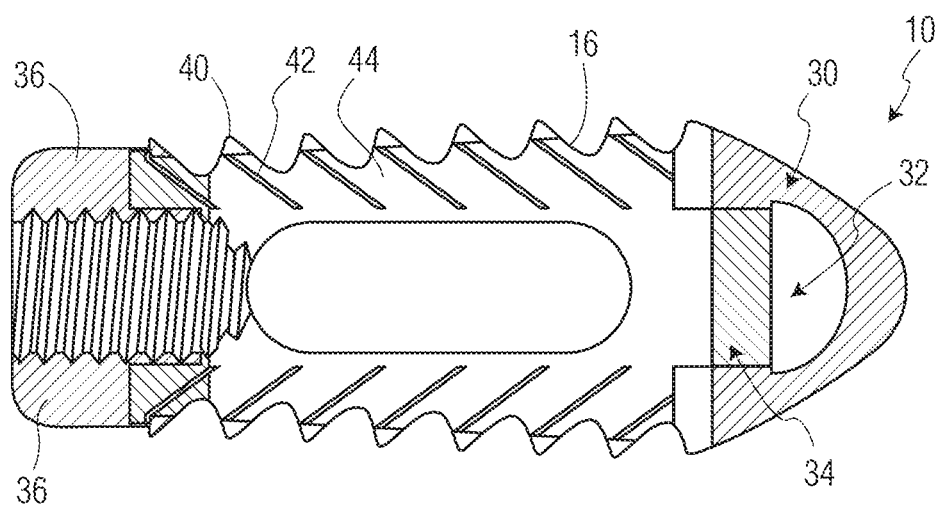
FIG. 6 is a cross-sectional view of the implant of FIG. 1 take along line 6-6 of FIG. 5.

With specific reference to FIGS. 2B, 4B and 6-8B, the location of the porous and solid portions of implant 10 will be discussed. In the solid model views of FIGS. 2B and 4B, the porous portions of the implant are shown as darker sections, while the solid portions are depicted in lighter material. The cross-sectional views of FIGS. 6-8B on the other hand depict these portions with different cross hatching. For instance, nose 20 includes a solid, smooth exterior construction. The use of solid metal in this section allows for it to withstand impaction loads during an insertion process, as well as for visualization of its location under fluoroscopy or other imaging. It is shown in FIG. 6 that nose 20 in actuality includes a solid portion 30, a hollow area 32 and a porous region 34. Solid portion 30 is designed to provide the necessary support discussed above, while hollow area 32 is provided in order to decrease the radioopacity of the nose and improve visualization under fluoroscopy imaging. Porous region 34, as will be discussed more fully below, extends into the area within cavity 18. It is contemplated that in other embodiments, porous region 34 may extend partially or completely into hollow area 32. This still acts to decrease the radioopacity of the nose, which improves visualization, but also improve the cleanability, sterilization and powder removal from the implant during processing.

Figure 8A:
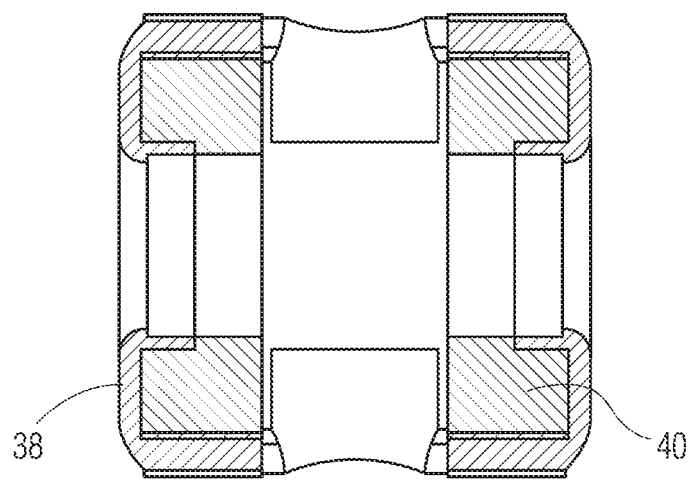
FIGS. 8A-8B are cross-sectional views of the implant of FIG. 1 take along lines 8A-8A and 8B-8B of FIGS. 4A and 4B, respectively.
Figure 8B:
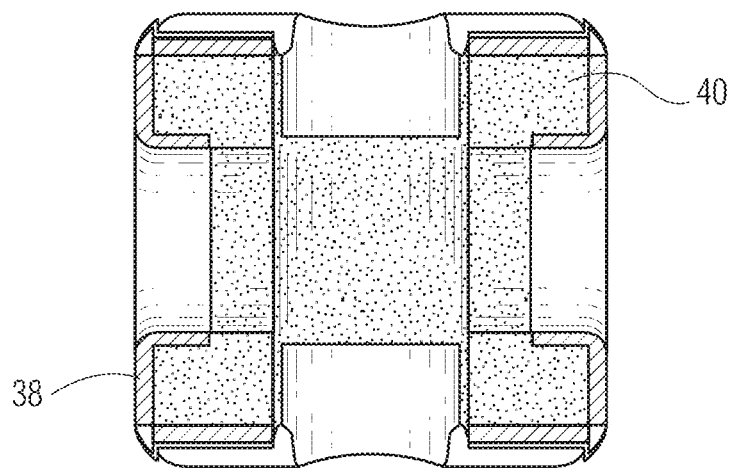

Like nose 20, a significant portion of rear end 22 is formed of solid material, so as to facilitate a strong connection with an insertion tool (not shown in detail). In particular, it is noted that while certain portions of the upper and lower surfaces 12, 14 at the rear end are porous, sections 36 are formed solid as they overlie threaded opening 24. This construction adds the necessary stability to the opening that is required for a solid connection with the insertion tool. Moreover, side walls 26, 28 are, as is best shown in FIGS. 8A and 8B, formed solid on an exterior of implant 10 and porous in an interior thereof. Specifically, with reference to FIG. 8B, the side walls include solid portions 38 and porous portions 40. Again, the inclusion of solid portions 38 provides stability to implant 10. However, as is mentioned above, lateral windows 27, 29 reduce the stiffness of the implant. Solid portions 38 may be any thickness, for instance, within the range of 0.25 mm to 0.5 mm. The solid portions also serve to provide a smooth exterior surface to the implant, which reduces tissue damage during implantation. It is noted that in certain embodiments, material may be machined off of any of the surfaces to create a smooth surface finish, which may further prevent tissue damage during implantation. This is especially true in connection with implanted formed by 3D printing processes, as such often result in even solid portions having a rougher surface finish.

Figure 7:
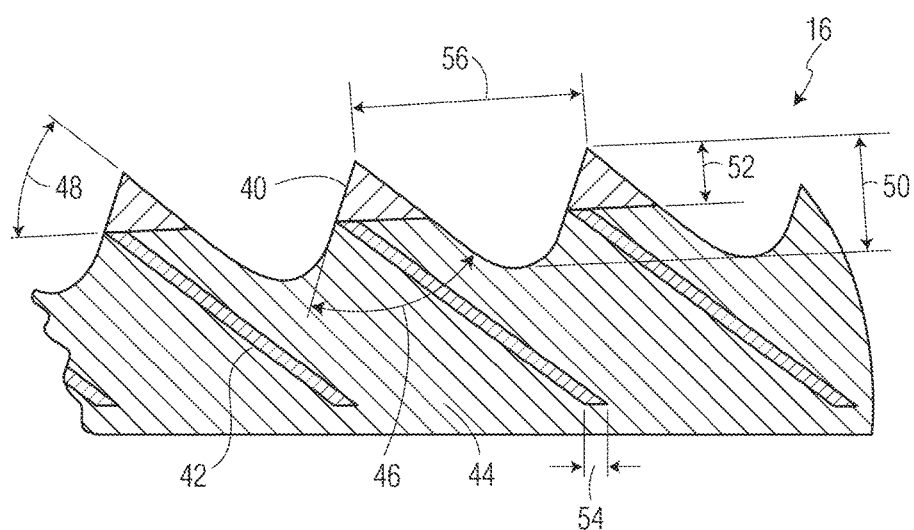
FIG. 7 is an enlarged cross-sectional view of serrations of the implant of FIG. 1.

Aside from the above discussed portions that are formed solid, the majority of the remainder of implant 10 is formed porous. Most notably, upper and lower surfaces 12, 14 are largely porous, especially in the portions having serrations 16. However, the serrations themselves include some solid portions. With reference to FIGS. 6 and 7, serrations 16 include solid tips 40 and solid roots 42, with the remainder of their construction including porous sections 44. Solid tips 40 not only provide a strong leading surface for engagement with bone, but also prevent fracture of a porous surface from occurring upon such engagement. Specifically, since the individual components (e.g., struts) of the porous surfaces of implant 10 may not necessarily converge to a point, they may fracture upon application of a force like what would be transmitted to serrations 16 during implantation. Solid core 42 also acts to strengthen serrations 16, by essentially providing a strong foundation for porous sections 44.

The particular shape of serrations 16 is also designed to create a strong initial implant-bone connection, while also allowing for easy insertion of implant 10 into the space between vertebrae. In order to resist back-out of implant 10, serrations 16 are oriented at an angle 46 (see FIG. 7). This angle may be any value, although a value within the range of 60 to 80 degrees is preferable. The angle 48 (see FIG. 7) of solid tips 40 is preferably in the range of 30 to 50 degrees. The height 50 of serrations 60 may be within the range of 0.5 mm to 1.5 mm, while the height 52 of solid tips 40 is dependent upon height 50, but preferably is within the range of 0.25 mm to 0.5 mm. Solid core 42 has a thickness 54, preferably 0.1 mm to 0.3 mm thick. The overall pitch 56 of serrations 16 is preferably between 1.25 mm and 2 mm.

Figure 9A:
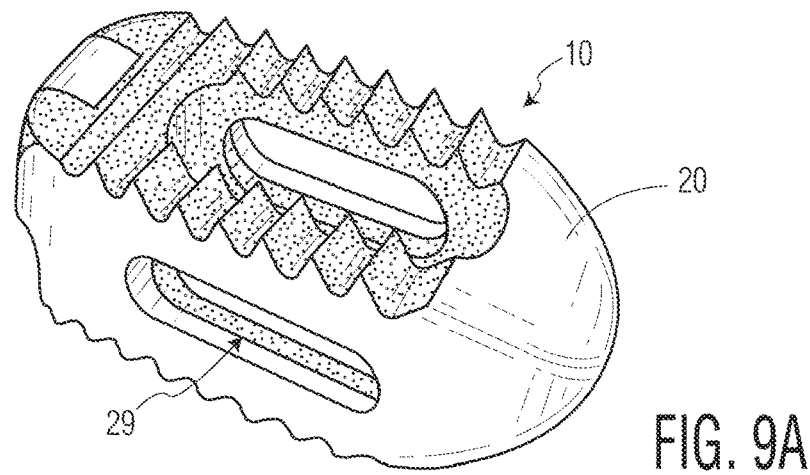
FIGS. 9A-9C are views illustrating a constructed version of the implant of FIG. 1.
Figure 9B:
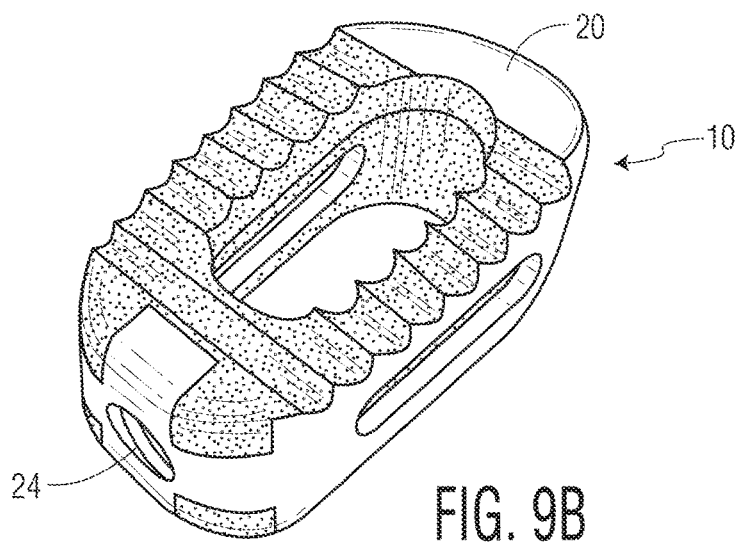
Figure 9C:
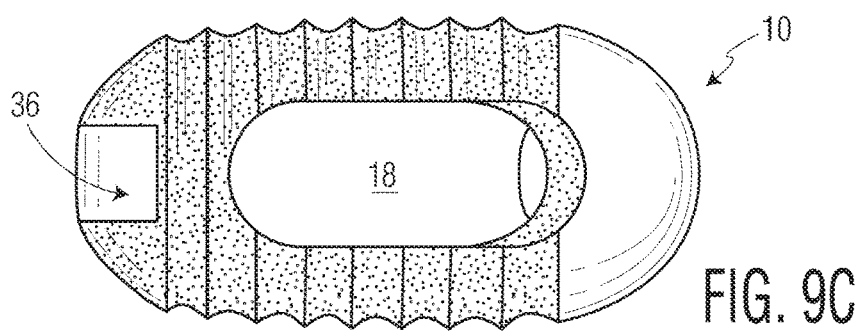

The interior of cavity 18 is largely constructed of porous material, which allows for bone growth in this section as well, and hence fusion through implant 10. This construction has the added benefit of also reducing stiffness of the implant, like lateral windows 27, 29. A fully constructed implant 10 is depicted in FIGS. 9A-9C. As shown, the various solid and porous portions of the implant appear differently to the naked eye. The particular prototype shown in those figures was created via a 3D printing process referred to as additive manufacturing, utilizing a titanium material. FIG. 10 is a fluoroscopic image of implant 10 while in position between two adjacent vertebral bodies. In the particular image shown there, implant 10 is engaged with an insertion tool 60, although the specifics of that tool cannot be seen.

Figure 11A:
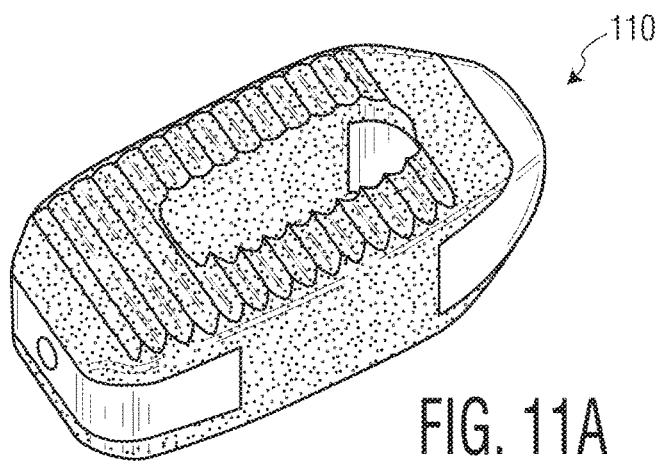
FIGS. 11A-11C are views of implants according to other embodiments of the present invention.
Figure 11B:
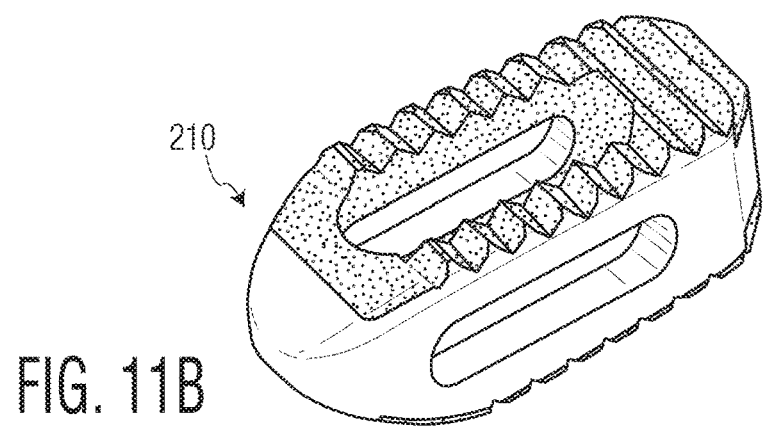
Figure 11C:
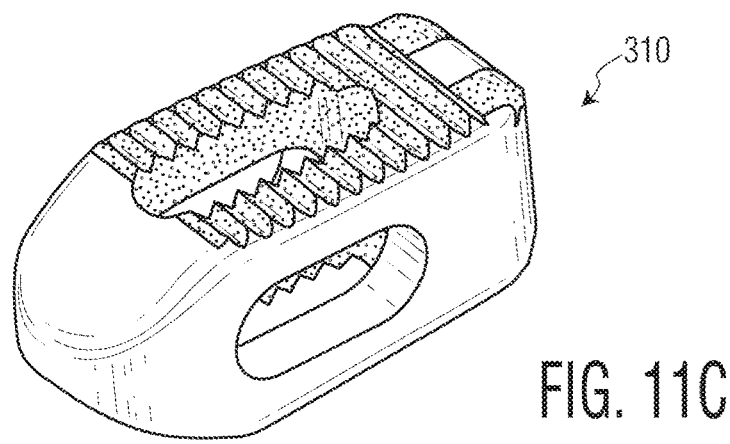
Figure 12A:
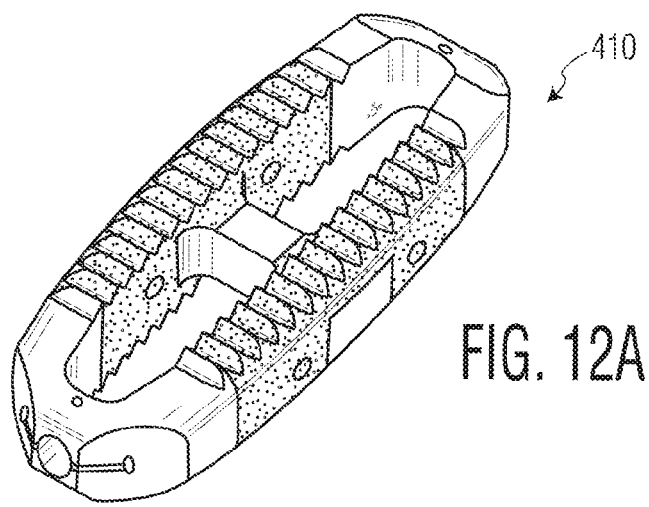
FIGS. 12A-12C are views of implants according to other embodiments of the present invention.
Figure 12B:
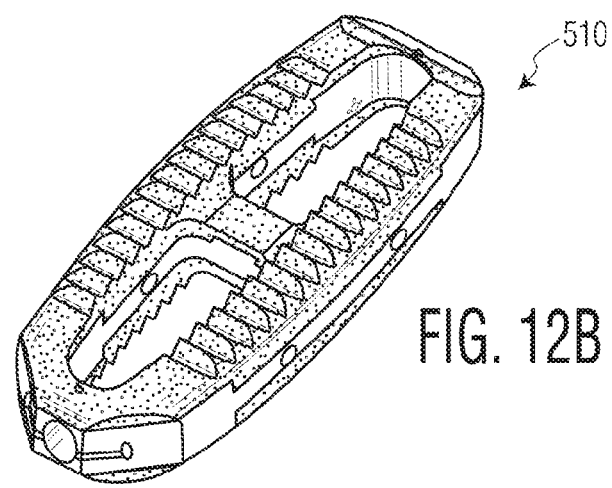
Figure 12C:
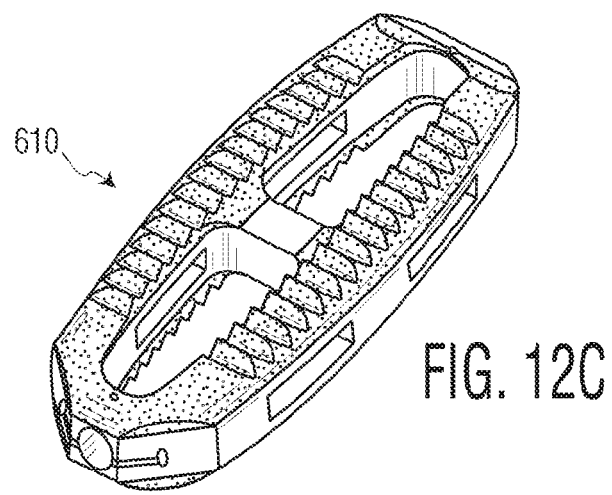
Figure 13A:
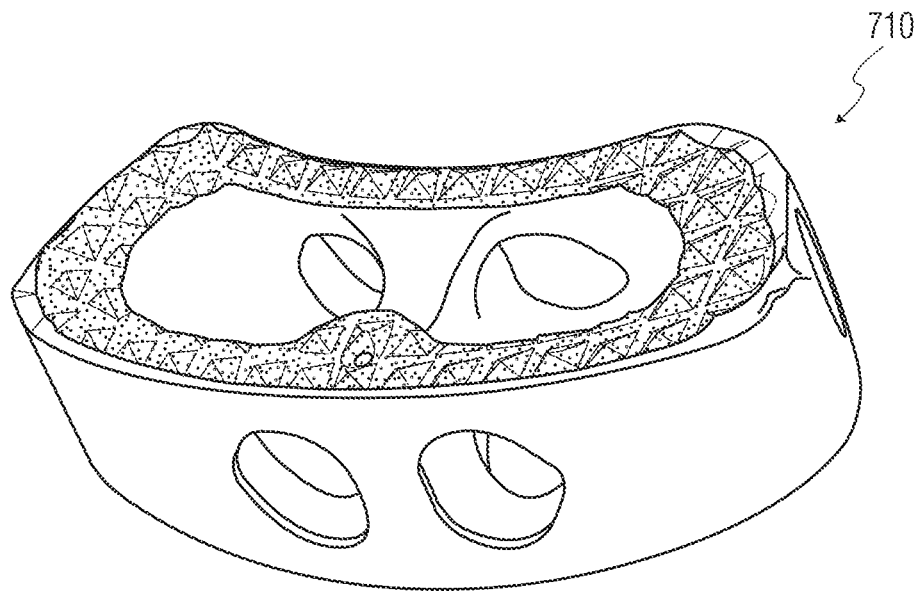
FIGS. 13A-13B are views of implants according to other embodiments of the present invention.
Figure 13B:
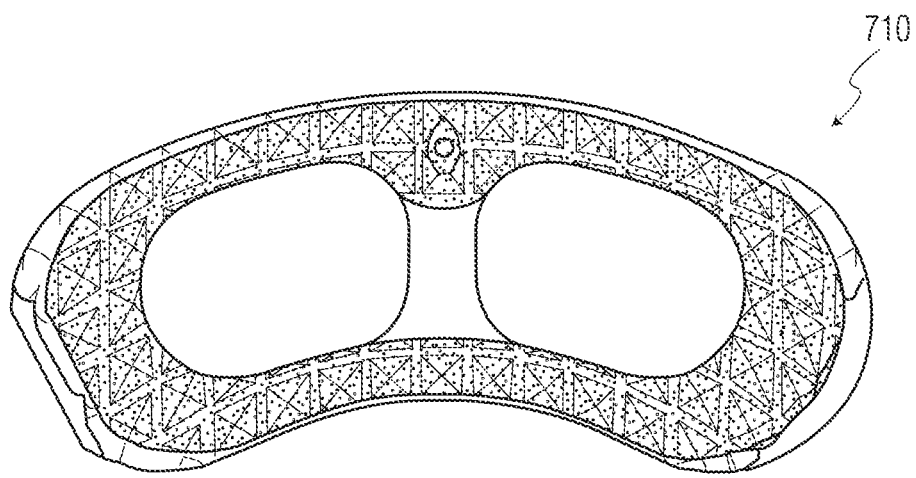
Figure 14A:
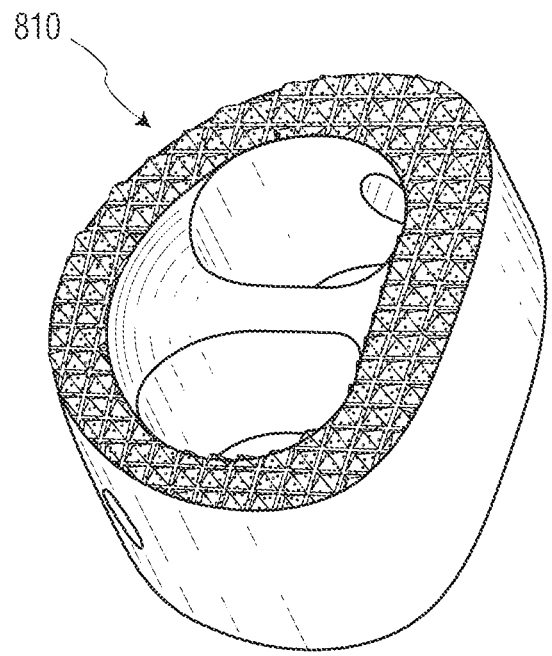
FIGS. 14A-14B are views of implants according to other embodiments of the present invention.
Figure 14B:
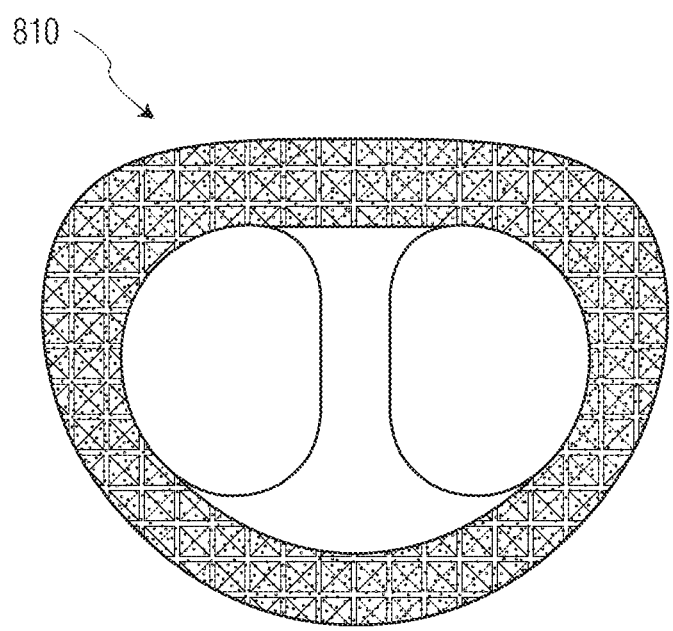

FIGS. 11A-11C depict different embodiment implants 110, 210 and 310, respectively that are each suitable for implantation from a posterior approach, like implant 10. FIGS. 12A-12C depict different embodiment implants 410, 510 and 610, respectively that are each suitable for implantation from a lateral approach. FIGS. 13A-13B depict an implant 710 suitable for implantation from a posterior lateral approach. FIGS. 14A-14B depict an implant 810 suitable for implantation from an anterior approach. Among other ways, those implants differ from implant 10 and each other in the manner in which their solid and porous portions are dispersed throughout the design. Again, solid portions are shown in lighter shading and porous portions are shown in darker shading. These various implant embodiments demonstrate that implants in accordance with the present invention may vary both in their size and shape, as well as in the configuration of their porous and solid portions.

Figure 15A:
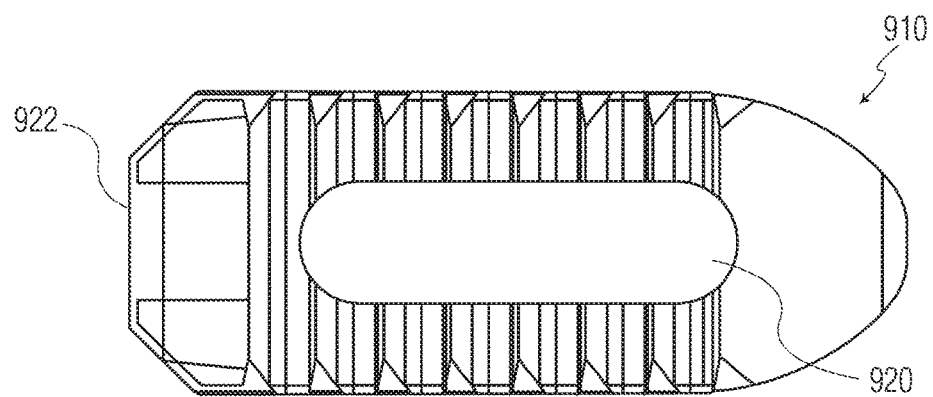
FIGS. 15A-15C are views of implants according to other embodiments of the present invention.
Figure 15B:
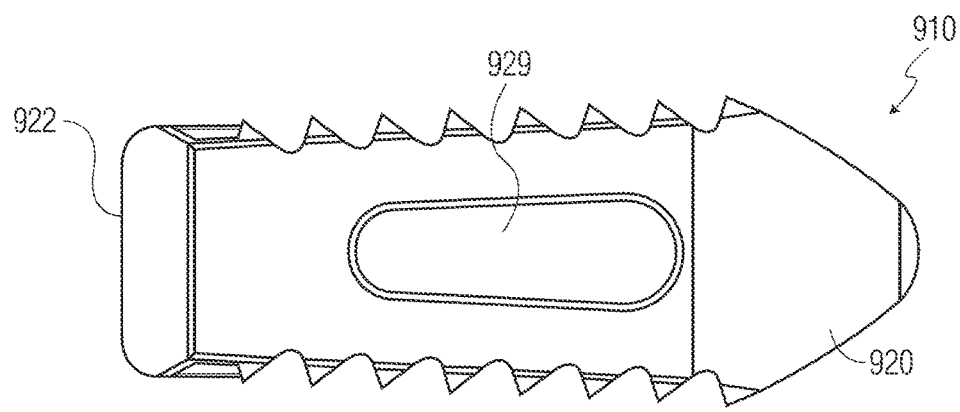
Figure 15C:
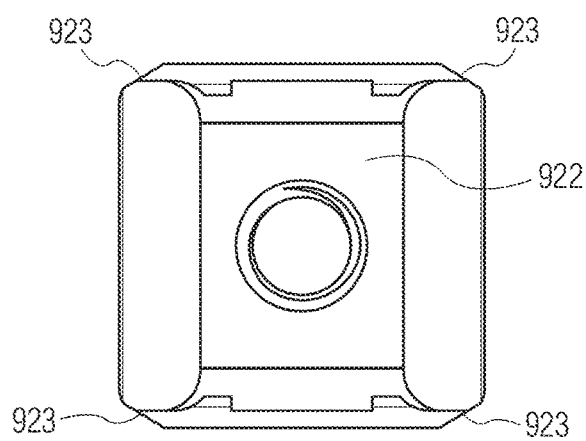

FIGS. 15A-15C depict an implant 910 similar to that of implant 10, albeit with certain specific differences. For instance, nose 920 includes sidewalls (best shown in FIG. 15A) that exhibit an increased angle from that of nose 20. This particular design allows for the implant to be inserted in an orientation that is rotated ninety degrees from the traditional insertion orientation of such an implant. Thereafter, implant 910 is rotated, which may result in an additional distraction from that of the initial insertion. Implant 910 may also be provided with a feature, such as a dimple or the like (not shown), that helps to identify the correct final orientation of the implant. For instance, a dimple may be provided at rear end 922 so that the surgeon may easily identify the final orientation of the implant. Of course, any visual identifier could also be employed.

Implant 910 also includes differently shaped/oriented lateral windows 927, 929 (only window 929 is shown in FIG. 15B) from that of above-discussed windows 27, 29. As shown, windows 927, 929 extend along less of implant 910 than do windows 27, 29 along implant 10. Moreover, the height of windows 927, 929 taper in the same direction as does the height of implant 910. For implants that are not lordotic, the windows may be a constant height. Finally, implant 910 exhibits chamfered edges 923 (best shown in FIG. 15C) that are on the four sides of the implant to eliminate sharp edges an make the implant more suitable for implantation without tissue damage.

Figure 16:
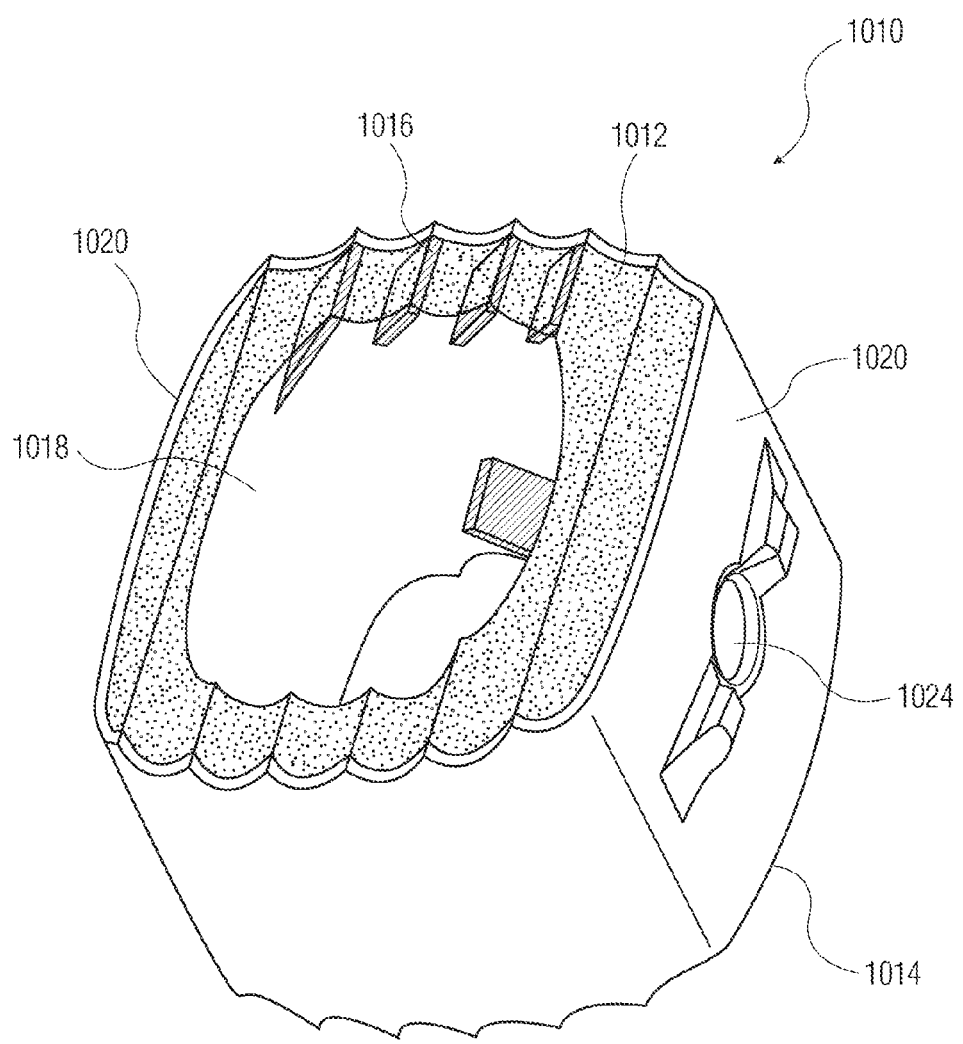
FIG. 16 depicts yet another implant according to another embodiment of the present invention.

FIG. 16 depicts yet another embodiment according to the present invention, cervical implant 1010. This implant is particularly suited for implantation in a cervical area of the spine and includes many elements similar to those of the other embodiment implants. For instance, implant 1010 includes upper and lower surfaces 1012, 1014 which include serrations 1016 similar to those discussed above. Further, the cervical implant includes a tapered nose or leading end 1020 and a trailing end 1022 with an aperture 1024 for engaging an insertion tool. Although other embodiments may vary, implant 1010 is shown as having porous portions at the upper and lower surfaces 1012, 1014 that are similar to those discussed above.

In use, the various implants in accordance with the present invention may be implanted in a manner similar to existing spinal implants. For instance, an insertion tool (e.g., tool 60) may be coupled with the implant to guide the implant into place between vertebral bodies. Initial engagement of the implant with the vertebral bodies is achieved via mechanical coupling elements included on the implant (e.g., serrations 16). Thereafter, bone is permitted to grow into any porous sections on the implant. This bone growth may be promoted through the use of bone growth promoting substances, such as allograft materials placed within cavity 18. After some time, the porosity of the implant preferably allows for a stronger fusion than that of existing, nonporous implants.

In creating an implant such as implant 10, the aforementioned 3D printing process can be utilized (see e.g., FIGS. 9A-9C). Because of the construction of the implant, it may be beneficial to orient the construction in one manner or the like. For instance, it has been found that orienting the build so that nose 20 faces down (i.e., is built first) results in better serration 16 creation. Of course, the nose down orientation is only one of many that can be employed and the creation of implants according to the present invention is not to be so limited.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A spinal implant comprising:
an upper surface including a first porous portion and first solid portion;
a lower surface including a second porous portion and a second solid portion;
a cavity formed through the upper and lower surfaces, the cavity including a third porous portion; and
at least one serration on each of the upper and lower surfaces, the at least one serration including a solid tip, a solid root and a porous section, the solid root extending away from the solid tip and defining a length greater than a thickness of the solid root.

2. The spinal implant of claim 1, further including first and second side walls extending between the upper and lower surfaces, the side walls including a solid exterior surface and a porous interior surface.

3. The spinal implant of claim 2, wherein the first and second side walls each include lateral windows.

4. The spinal implant of claim 3, wherein the lateral windows reduce the stiffness of the implant.

5. The spinal implant of claim 4, wherein the lateral windows taper.

6. The spinal implant of claim 1, further comprising a threaded opening at a rear end.

7. The spinal implant of claim 1, wherein the implant is constructed of a metal.

8. The spinal implant of claim 7, wherein the metal is titanium.

9. The spinal implant of claim 1, wherein the implant is configured for insertion from a posterior approach, a lateral approach or an anterior approach.

10. The spinal implant of claim 1, further including a nose that facilitates the insertion of the implant in a first orientation and rotation to a second orientation.

11. The spinal implant of claim 10, wherein the nose has a solid exterior.

12. The spinal implant of claim 1, wherein the implant is constructed from an additive manufacturing process.

13. The spinal implant of claim 12, wherein the implant is machined to create smooth surfaces.

\* \* \* \* \*